United States Patent [19]

Pittz et al.

[11] Patent Number: 4,672,076
[45] Date of Patent: Jun. 9, 1987

[54] NON-STEROIDAL ANTI-INFLAMMATORY COMPOUNDS AND COMPOSITIONS THEREOF

[75] Inventors: Eugene P. Pittz, Randolph; Richard V. Smerbeck, Hackettstown, both of N.J.

[73] Assignee: Warner-Lambert Company, Morris Plains, N.J.

[21] Appl. No.: 604,789

[22] Filed: Apr. 27, 1984

[51] Int. Cl.$^4$ .............................................. C07L 69/76
[52] U.S. Cl. ...................... 514/544; 560/72; 560/73
[58] Field of Search ...................... 560/72, 73; 514/544

[56] References Cited

U.S. PATENT DOCUMENTS

| | | | |
|---|---|---|---|
| 3,642,865 | 2/1972 | Diamond et al. | 560/19 |
| 3,714,227 | 1/1973 | Ueno et al. | 560/60 |
| 4,373,953 | 2/1983 | Deinet et al. | 106/16 |

FOREIGN PATENT DOCUMENTS

| | | |
|---|---|---|
| 0027286 | 4/1981 | European Pat. Off. |
| 0028063 | 5/1981 | European Pat. Off. |
| 41820 | 9/1981 | Japan . |
| 85820 | 5/1983 | Japan . |
| 1279039 | 6/1972 | United Kingdom . |

OTHER PUBLICATIONS

Abraham, D. et al, J. Med. Chem., 1984, 27(12), 1549-1559.
Asakawa, H. et al, Chem. Pharm. Bull., 1979, 27(2), 522-527.

*Primary Examiner*—Paul J. Killos
*Attorney, Agent, or Firm*—Howard Olevsky; Gary M. Nath

[57] ABSTRACT

A non-steroidal anti-inflammatory composition comprising an active anti-inflammatory agent having the formula:

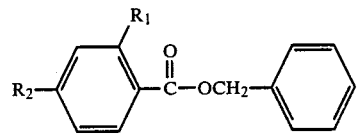

wherein $R_1$ and $R_2$ are hydrogen hydroxy. The active agent is formulated with a pharmaceutically acceptable carrier for use in the treatment of pain, inflammation and other related symptoms on mammals. Benzyl paraben, benzyl salicylate and benzyl benzoate are preferred.

10 Claims, No Drawings

NON-STEROIDAL ANTI-INFLAMMATORY COMPOUNDS AND COMPOSITIONS THEREOF

The present invention relates to non-steroidal anti-inflammatory compounds useful as active agents in the treatment of pain, inflammation, swelling and other related symptoms of mammals. This invention also relates to pharmaceutically acceptable compositions containing these actives as well as a method of treatment.

Non-steroidal anti-inflammatory compounds are well-known in the art. Examples of such compounds are aspirin, indomethacin, and phenylbutazone, to name a few. All of these have claims associated with them for the treatment of pain and inflammation in mammals. These compounds are known to cause side-effects, gastroenteric disorders and headaches.

U.S. Pat. No. 4,145,444 to Hamazaki et al., discloses various non-carboxylic benzoyl derivatives as anti-inflammatory agents. In particular, those compounds disclosed have the formula

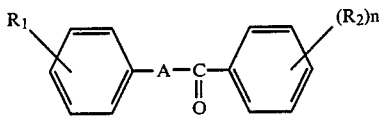

wherein $R_1$ represents hydrogen, halogen, hydroxy, $C_{1-8}$ alkyl or $C_{1-8}$ alkoxy; $R_2$ represents hydrogen, halogen, hydroxy, vinyl, $C_{1-8}$ alkyl or $C_{1-8}$ alkoxy; A represents carbonyl, methylene or a single bond; and n is an integer of 1 to 4. It is preferred that $R_2$ be n-butyl substituted in the ortho or para position, and $R_1$ be hydrogen or halogen, e.g., compounds having the chemical name 4-n-butylbenzophenone or 4-n-butyl-2'-fluorobenzophenone.

U.S. Pat. No. 4,244,970 to Dewhirst discloses a method of treating inflammation and inhibiting prostaglandin synthesis by administering an effective amount of 2-hydroxybenzophenone and substitutes thereof. This patent discloses only those compounds having one hydroxy group located at the ortho position on at least one of the benzene rings.

The association between the production of prostaglandins in mammals and inflammation and pain is well documented. See Greaves and Sondergaard, Journal of Investigative Dermatology 72:59–63, 1979, where it was first demonstrated that prostaglandin activity was present in tissue fluid taken from inflamed human skin. Other investigators have subsequently reported that $PGE_2$ (prostaglandin $E_2$) concentrations in skin increase after exposure to ultraviolet (UVB) light and mediate a significant degree of redness and inflammation, particularly in the first 24 hours subsequent to exposure.

Without wishing to be bound by any one theory, it is believed that the inventive compounds and compositions based thereon, particularly those containing benzyl salicylate, benzyl paraben and benzyl benzoate, are effective prostaglandin inhibitors. It is theorized that the effective inhibition of prostaglandin synthesis is the mechanism by which the novel compounds reduce and control pain and inflammation in mammals.

The literature has clearly shown that non-steroidal anti-inflammatory agents will reduce ultraviolet induced erythema by inhibiting the production of prostaglandin $E_2$ within the first 24 hour period subsequent to UVB exposure. See "Prostaglandins in the Skin," by Neal S. Penneys, published by Upjohn Co., 1980.

It is apparent that there is a need for effective, novel non-steroidal anti-inflammatory compounds which can be formulated into compositions using pharmaceutically acceptable carriers for topical, rectal, oral, perlingual or parenteral administration. The novel, instant compounds fulfill this need.

The instant invention relates particularly to the use of the compound having the structural formula below:

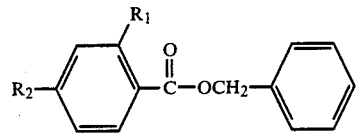

wherein $R_1$ and $R_2$ represent hydrogen or hydroxy.

When $R_1$ is a hydroxy group, and $R_2$ is hydrogen, the compound is commonly known as benzyl salicylate. When $R_1$, and $R_2$ are both hydrogens, the compound is commonly known as benzyl benzoate. When $R_1$ is hydrogen and $R_2$ is an hydroxy group, the compound is known as benzyl paraben, or alternatively benzyl-p-hydroxybenzoate. These compounds, alone or in combination, are useful in relieving pain and inflammation.

While these compounds were previously known, heretofore they have not been disclosed as anti-inflammatory or pain relieving compounds. Benzyl paraben is often used as a preservative in dermatological preparations. Benzyl benzoate is often used as a fixative agent for perfumes and scabicide (page 1137, 9th edition Merck Index). Benzyl salicylate is also known as a fixative agent for perfume and as a sunscreen (page 1168, 9th edition Merck Index).

The inventive compounds, when administered in therapeutically effective amounts, either alone or in a pharmaceutically acceptable carrier, are effective as a remedy for pain, inflammation and other related symptoms in mammals.

The instant compounds are generally used in a therapeuticaly effective amount, but when contained in a pharmaceutically acceptable carrier or composition, are generally present in amounts of about 0.05% to about 35% by weight of the composition; preferably in amounts of about 0.1% to about 15% and most preferably about 0.1% to about 1% by weight of the composition.

The inventive compounds are preferably used in a composition which can be easily and conveniently administered to a mammal experiencing pain and inflammation. As mentioned above, dosage forms may be varied and include topical creams, pastes, ointments, gels, lotions and the like, for direct application to the inflammed area. Oral dosage forms include, but are not limited to capsules, tablets, solutions, syrups, powders and the like. Rectal, perlingual and parenteral dosage forms are also contemplated.

The instant compounds and their compositions are intended for use in the treatment of a variety of inflammatory problems and diseases including systemic diseases such as arthritis and the like.

The preferred dosage form is a topical lotion comprising the inventive compounds or mixtures thereof in a pharmaceutically acceptable carrier. Illustrations of useful carriers include ethanol and other lower alkyl alcohols, polyalcohols, mineral oils, vegetable oils, petrolatum, glycerine, nonionic surfactants, water and the like, as well as mixtures of these. Compositions comprising from about 0.05% to about 20% by weight of the inventive compounds in the above carriers have been found particularly effective in the treatment of inflammation of the skin, commonly known in the art as erythema.

The active anti-inflammatory compounds of the instant invention can be applied together with other anti-inflammatory agents, analgesics, thrombus dissolving agents, thrombus inhibiting agents, antibiotics and the like.

In the case where the active compounds are incorporated in a pharmaceutical composition, other common materials such as lubricants, humectants, surfactants, waxes, emulsifiers, thickeners, emollients, preservatives, demulcents, perfumes, coloring additives and the like may be added. These, of course, are not critical to the invention and their amounts can be varied and balanced to meet the desired properties of the overall composition, which is discoverable by routine experimentation by one skilled in the art.

The instant compositions may include materials that serve as occlusives in that they hold moisture against the surface of the skin. Suitable occlusive compounds include cetyl alcohol, cetyl palmitate, petrolatum, mineral oil and the like. These materials are generally present in topical compositions, for example, in amounts of about 1% to about 5 25% by weight of the composition and preferably in amounts of about 2% to about 10%.

A variety of materials may be utilized as emulsifiers, including high molecular weight polyethylene glycols, fatty alcohols such as stearyl alcohol and myristyl alcohol and the like. These materials are generally present in amounts of about 0.1% to about 15% by weight of the composition and preferably in amounts of about 1% to about 10%.

Suitable emollients for use in the instant compositions containing the novel anti-inflammatory compounds include fatty acid esters such as cetyl palmitate, diisopropyl adipate, isopropyl isostearate, isostearyl isostearate and mixtures thereof, to name a few. Generally they are present in topical compositions in amounts of about 0.1% to about 20% by weight of the composition and preferably in amounts of about 1% to about 10%.

Suitable humectants may be any of those well known in the art. Examples of useful humectants include glycerin, propylene glycol, polyethylene glycol, polyhydric alcohols and mixtures thereof, to name a few. Preferably, glycerin is used. These materials may be incorporated in the inventive anti-inflammatory compositions in amounts of about 0.1% to about 30% by weight of the composition and preferably in amounts of about 3% to about 20%.

Numerous surfactants, and preferably non-ionic surfactants, may be added for their intended purpose. Among those preferred are polyalkanolamines such as triethanolamine, polyethylene glycol stearate, polyethylene glycol laurate, polyoxyethylene and polyoxypropylene compounds, e.g. as derivatives of sorbitan and fatty alcohol esters, fatty acid esters of polyhydric alcohols and amine oxides; anionic surfactants, such as alkyl carboxylates, acyl lactylates, sulfuric acid esters (e.g. sodium lauryl sulfate), 5 ester-linked sulfonates, and phosphated ethoxylated alcohols; cationic surfactants, such as monoalkyl and dialkyl quaternary ammonium salts, amidoamides and aminimides. These various surfactants, when compatable, can be added as mixtures to the instant compositions and are generally present in amounts of about 0.1% to about 15% by weight of the composition.

Lubricating agents may be used when desired in the instant compositions. They include silicone oils or fluids such as substituted and unsubstituted polysiloxanes, e.g. dimethyl polysiloxane, also known as dimethicone, is particularly useful when the composition is to be used as a topical preparation. The lubricating agents, when incorporated in a topical composition, are generally present in amounts of about 0.1% to about 30% by weight of the composition and preferably in amounts of about 1% to about 10%. Other lubricating agents well known to the tableting and capsule art may be used when the dosage form is a tablet, pill or capsule. These lubricating agents are primarily to aid in formation of tablets.

Preservatives such as alkyl and aryl parabens and substituted phenols are also useful additives. Examples of the preferred parabens are the methyl, propyl and butyl parabens useful in ranges of 0.1 to about 0.25%. In a preferred embodiment, a combination of methyl, propyl and butyl paraben may be used in the respective ranges of about 0.1% to about 0.25%, 0.02% to about 0.2% and 0 to about 0.05%. Examples of the useful substituted phenols include chloro-substituted phenoxy phenols, such as 5-chloro-2-(2,4-dichlorophenoxy)-phenol, hexachlorophene, triclosan and dichlorophene, among others.

Other useful preservatives include mercury derivatives, such as phenylmercuric acetate; quarternaries, such as benzethonium chloride, benzalkonium chlorides and cetyl trimethyl ammonium bromide; acids, such as sorbic acid; and a variety of other preservatives such as Kathon CG, a trademark of Rohm & Haas Co. which comprises a mixture of 5-chloro-2-methyl-4-isothiazolin-3-one and 2-methyl-4-isothiazolin-3-one.

Other conventional additives may be utilized, such as fragrance oils, thickeners, emulsifiers and other additives. For example, in the case of a topical lotion, thickeners for viscosity adjustment would include xanthan gum, sodium stearyl sulfate, and materials of that type.

The foregoing recitation of materials is presented for purposes of illustration and not limitation, it being understood that a variety of equivalent materials would all function in the capacities set forth above.

The instant invention also includes a method of treatment for inflammation, pain and related symptoms whereby a mammal is administered a therapeutically effective amount of the compound having the structural formula:

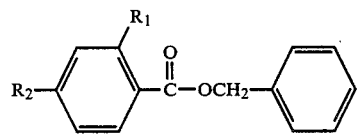

wherein $R_1$ and $R_2$ is hydrogen or a hydroxy group.

The invention will be further appreciated by the following example which is intended to illustrate an embodiment of the instant invention. All percentages throughout the specification are by weight of the total composition unless otherwise indicated.

EXAMPLE

This example is designed after the guinea pig model of Snyder, Journal of Investigative Dermatology, 64: 322-25, 1975, and demonstrates that skin inflamed by ultraviolet light (U.V.B.) can be effectively therapeutically treated using a compound of the instant invention. Additionally, this example demonstrates that the instant compounds when applied topically in a dermatological preparation are effective in inhibiting the production of prostaglandins which are believed to be responsible for the inflammation.

The dorsal surface of a male albino guinea pig was shaved with a standard animal clipper (#40 head), depilated with a commercially available thioglycolate based depilatory product, rinsed with tap water and dried. The animal was immobilized in a standard head stock and irradiated for 30 minutes. This period of irradiation was found to be equivalent 3 MED's. An MED (minimum erythemal dose) is the minimal amount of U.V.B. radiation required to produce sunburn 24 hours subsequent to exposure. The U.V.B. light source was a bank of Westinghouse FS-40 lamps.

Immediately after irradiation, the animal's exposed dorsal surface was delineated with a black marking pen into treatment sites. Some sites were then treated with ten (10) micro-liters of benzyl paraben (3% solution) a preferred embodiment of the instant invention. Additional cites were treated with ten (10) micro-liters of benzyl salicylate (3% solution) and ten (10) microliters of benzyl benzoate (3% solution) respectively, also preferred embodiments of the instant invention. Other areas were treated with a substituted 2-hydroxybenzophenone (3% solution) compound as a control, this compound being disclosed in 30 U.S. Pat. No. 4,244,970 to Dewhurst. The sites were then visually evaluated for lack of erythema (blanching) at 1, 5 and 24 hours post-treatment by a trained, doubleblinded observer. The results, as described below, were based on the following scale:

0—No Blanching
1—Barely Detectable Blanching
2—Moderate Blanching
3—Severe Blanching
4—Complete Blanching (no erythema)

The results are tabulated below:

| Agent | Vehicle | Blanching Score | | |
|---|---|---|---|---|
| | | 1 hr. | 5 hrs. | 24 hrs. |
| benzyl benzoate (3%) | PG:EtOH:DMA* | 1+ | 0 | 0 |
| benzyl paraben (3%) | PG:EtOH:DMA | 1+ | 1 | 0 |
| benzyl salicylate (3%) | PG:EtOH:DMA | 1+ | 1+ | 0 |
| Control (3%)** | PG:EtOH:DMA | 1+ | 1+ | 0 |

*Propylene glycol:ethanol:N,N—dimethylacetamide (19:19:2)
**Percents on a weight/weight basis of total product (vehicle and agent).

These results indicate that post-irradiation application of a compound of the instant invention inhibits prostaglandin production as indicated by the reduction of inflammation evidenced by blanching.

The invention being thus described, it will be obvious that the same may be varied in many ways. Such variations are not to be regarded as a departure from the spirit and scope of the invention and all such modifications are intended to be included within the scope of the claims.

What is claimed is:

1. A method for the treatment of inflammation in mammals comprising administering a therapeutically effective amount of a compound having the formula:

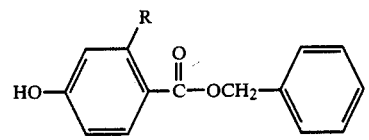

wherein R is hydrogen or hydroxy.

2. The method of claim 1 further comprising applying the compound in a topical preparation to the area of pain or inflammation.

3. The method of claim 1 further comprising administering the compound orally.

4. The method of claim 1 further comprising applying the compound rectally.

5. The method of claim 1 further comprising administering the compound perlingually or parenterally.

6. The method of claim 2 further comprising applying the compound topically in a pharmaceutically acceptable carrier.

7. The method of claim 6 wherein $R_1$ and $R_2$ are hydrogen.

8. The method of claim 6 wherein $R_1$ is hydrogen and $R_2$ is hydroxy.

9. The method of claim 6 wherein $R_1$ is hydroxy and $R_2$ is hydrogen.

10. The method of claims 7, 8 or 9 wherein the pharmaceutically acceptable carrier is present in amounts up to about 99% and the compound is present in amounts of about 0.05% to about 20%, percents based on the weight of the total composition.

* * * * *